(12) United States Patent
Katz et al.

(10) Patent No.: US 12,014,496 B2
(45) Date of Patent: Jun. 18, 2024

(54) DETECTION OF ARTIFACTS IN MEDICAL IMAGES

(71) Applicant: NEC Corporation Of America, Herzlia (IL)

(72) Inventors: Or Katz, Ganei Tikva (IL); Liz Cohen, Tiberias (IL); Yaacov Hoch, Ramat-Gan (IL); Dan Presil, Givatayim (IL)

(73) Assignee: NEC Corporation Of America, Herzlia (IL)

( * ) Notice: Subject to any disclaimer, the term of this patent is extended or adjusted under 35 U.S.C. 154(b) by 366 days.

(21) Appl. No.: 17/568,844

(22) Filed: Jan. 5, 2022

(65) Prior Publication Data
US 2023/0214993 A1 Jul. 6, 2023

(51) Int. Cl.
| | |
|---|---|
| *G06T 7/00* | (2017.01) |
| *G06T 5/77* | (2024.01) |
| *G06T 7/11* | (2017.01) |
| *G06V 10/75* | (2022.01) |
| *G06V 10/764* | (2022.01) |
| *G06V 10/77* | (2022.01) |
| *G06V 10/771* | (2022.01) |
| *G06V 10/82* | (2022.01) |
| *G06V 10/98* | (2022.01) |

(Continued)

(52) U.S. Cl.
CPC ............. *G06T 7/0012* (2013.01); *G06T 5/77* (2024.01); *G06T 7/11* (2017.01); *G06V 10/751* (2022.01); *G06V 10/764* (2022.01); *G06V 10/771* (2022.01); *G06V 10/7715* (2022.01); *G06V 10/82* (2022.01); *G06V 10/993* (2022.01); *G16H 30/40* (2018.01); *G16H 50/20* (2018.01); *G06T 2207/10024* (2013.01); *G06T 2207/20081* (2013.01); *G06T 2207/20084* (2013.01); *G06T 2207/30041* (2013.01); *G06T 2207/30096* (2013.01); *G06T 2207/30168* (2013.01); *G06V 2201/03* (2022.01)

(58) Field of Classification Search
CPC G06T 7/0012; G06T 7/11; G06T 5/77; G16H 50/20; G16H 30/40; G06V 10/771; G06V 10/7715; G06V 10/82; G06V 10/751; G06V 10/993; G06V 10/764
See application file for complete search history.

(56) References Cited

U.S. PATENT DOCUMENTS

2023/0135995 A1* 5/2023 Chen .................... A61B 5/7257 382/131

* cited by examiner

*Primary Examiner* — David Perlman (57) ABSTRACT

There is provided a method of re-classifying a clinically significant feature of a medical image as an artifact, comprising: feeding a target medical image captured by a specific medical imaging sensor at a specific setup into a machine learning model, obtaining a target feature map as an outcome of the machine learning model, wherein the target feature map includes target features classified as clinically significant, analyzing the target feature map with respect to sample feature map(s) obtained as an outcome of the machine learning model fed a sample medical image captured by at least one of: the same specific medical imaging sensor and the same specific setup, wherein the sample feature map(s) includes sample features classified as clinically significant, identifying target feature(s) depicted in the target feature map having attributes matching sample feature (s) depicted in the sample feature map(s), and re-classifying the identified target feature(s) as an artifact.

20 Claims, 4 Drawing Sheets

(51) Int. Cl.
 *G16H 30/40* (2018.01)
 *G16H 50/20* (2018.01)

DETECTION OF ARTIFACTS IN MEDICAL IMAGES

BACKGROUND

The present invention, in some embodiments thereof, relates to medical image processing and, more specifically, but not exclusively, to detection of artifacts in medical images.

In modern medicine, imaging is vitally important. X-rays, ultrasound, CT scans, and MRI are examples of modern imaging techniques that display structures inside the body in remarkable detail.

Artifacts may appear in medical images generated by the imaging modalities. Artifacts seen on a medical image are not present in reality in the body of the patient, but appear due to a quirk of the modality capturing the modality.

SUMMARY

According to a first aspect, a computer implemented method of re-classifying a clinically significant feature of a medical image as an artifact, comprising: feeding a target medical image captured by a specific medical imaging sensor at a specific setup into a machine learning model, obtaining a target feature map as an outcome of the machine learning model, wherein the target feature map includes target features classified as clinically significant by the machine learning model, analyzing the target feature map with respect to at least one sample feature map obtained as an outcome of the machine learning model fed a sample medical image captured by at least one of: the same specific medical imaging sensor and the same specific setup, wherein the at least one sample feature map includes sample features classified as clinically significant by the machine learning model, identifying at least one target feature depicted in the target feature map having attributes matching at least one sample feature depicted in the at least one sample feature map, and re-classifying as an artifact, the identified at least one target feature depicted in the target medical image and classified as clinically significant by the machine learning model.

According to a second aspect, a device for re-classifying a clinically significant feature of a medical image as an artifact, comprises: at least one hardware processor executing a code for: feeding a target medical image captured by a specific medical imaging sensor at a specific setup into a machine learning model, obtaining a target feature map as an outcome of the machine learning model, wherein the target feature map includes target features classified as clinically significant by the machine learning model, analyzing the target feature map with respect to at least one sample feature map obtained as an outcome of the machine learning model fed a sample medical image captured by at least one of: the same specific medical imaging sensor and the same specific setup, wherein the at least one sample feature map includes sample features classified as clinically significant by the machine learning model, identifying at least one target feature depicted in the target feature map having attributes matching at least one sample feature depicted in the at least one sample feature map, and re-classifying as an artifact, the identified at least one target feature depicted in the target medical image and classified as clinically significant by the machine learning model.

According to a third aspect, a non-transitory medium storing program instructions for re-classifying a clinically significant feature of a medical image as an artifact, which, when executed by a processor, cause the processor to: feed a target medical image captured by a specific medical imaging sensor at a specific setup into a machine learning model, obtain a target feature map as an outcome of the machine learning model, wherein the target feature map includes target features classified as clinically significant by the machine learning model, analyze the target feature map with respect to at least one sample feature map obtained as an outcome of the machine learning model fed a sample medical image captured by at least one of: the same specific medical imaging sensor and the same specific setup, wherein the at least one sample feature map includes sample features classified as clinically significant by the machine learning model, identify at least one target feature depicted in the target feature map having attributes matching at least one sample feature depicted in the at least one sample feature map, and re-classify as an artifact, the identified at least one target feature depicted in the target medical image and classified as clinically significant by the machine learning model.

In a further implementation form of the first, second, and third aspects, the target medical image and the sample medical images are at least one of: of different subjects, of different body parts of the same subject.

In a further implementation form of the first, second, and third aspects, the target feature map indicates attributes of each target feature identified by the machine learning model, the attributes including at least one of: (i) a location and (ii) at least one of a size and a shape of the respective target feature.

In a further implementation form of the first, second, and third aspects, the at least one target feature is identified when a specific feature of the target feature map has a same location, and at least one of a same size and a same shape, as a corresponding sample feature depicted in the at least one sample feature map.

In a further implementation form of the first, second, and third aspects, the target feature map is extracted from a hidden layer of a neural network implementation of the machine learning model.

In a further implementation form of the first, second, and third aspects, the target feature map comprises at least one of: bounding boxes delineating respective features, and segmentations delineating respective features applied to the target medical image, and identified pixels of the target medical image delineating respective features.

In a further implementation form of the first, second, and third aspects, analyzing comprises comparing the target feature map with the at least one sample feature map to identify a common feature appearing at a same location in the target feature map and in the at least one sample feature map.

In a further implementation form of the first, second, and third aspects, the target feature map is implemented as an image, and analyzing comprises comparing the image of the target feature map with at least one sample image of the at least one sample feature map to identify common features at a same location in the image of the target feature map and in the at least one sample image of the at least one sample feature map.

In a further implementation form of the first, second, and third aspects, the comparing comprises applying a feature matching process to the image of the target feature map and to the at least one sample image of the at least one sample feature map, to identify common features at the same location and same orientation.

In a further implementation form of the first, second, and third aspects, the identified at least one target feature re-classified as artifact is selected from a group consisting of: light reflected from an eye into a camera capturing the target medical image, dirt on a lens of the camera, malfunction of the specific medical imaging sensor, lighting problem captured by the specific medical imaging sensor.

In a further implementation form of the first, second, and third aspects, the target medical image comprises a retinal color fundus image, the specific medical imaging sensor comprises a camera, the machine learning model is trained to identify retinal lesions, and the clinically significant features include retinal lesion.

In a further implementation form of the first, second, and third aspects, the retinal lesions are selected from a group comprising: hard exudate, neovascularization on disk (NVD), neovascularization elsewhere (NVE), intraretinal microvascular abnormality (IRMA), venous bleeding, microaneurysm, and blot hemorrhage.

In a further implementation form of the first, second, and third aspects, the target medical image depicts a first body portion of a subject, and the sample medical image depicts a second body portion of the subject.

In a further implementation form of the first, second, and third aspects, the first body portion of the subject comprises a first eye of the subject, and the second body portion of the subject comprises a second eye of the subject.

In a further implementation form of the first, second, and third aspects, further comprising designating non-identified at least one target feature of the target feature map as clinically significant features.

In a further implementation form of the first, second, and third aspects, further comprising visually marking the identified at least one target feature designated as the artifact on the target medical image presented on a display.

In a further implementation form of the first, second, and third aspects, further comprising processing the target medical image identified as the artifact for removing the identified at least one target feature from the medical image.

In a further implementation form of the first, second, and third aspects, processing comprises replacing the identified at least one target feature of the target medical image identified as the artifact with a benign feature not identifiable by the machine learning model as a clinically significant feature.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

The present invention, in some embodiments thereof, relates to medical image processing and, more specifically, but not exclusively, to detection of artifacts in medical images.

An aspect of some embodiments of the present invention relates to systems, methods, devices, and/or code instructions (stored on a data storage device and executable by one or more processors) for re-classification of a clinically significant feature of a medical image detected by a machine learning model, as an artifact. The medical image may be, for example, a retinal color fundus image that may be used for diabetic retinopathy screening. A target medical image is fed into a machine learning (ML) model. The target medical image is captured by a specific medical imaging sensor (e.g., camera) at a specific setup (e.g., orientation and/or location relative to a subject). The machine learning model is trained to identify one or more target features depicted in the target medical image which are likely clinically significant, for example, retinal lesions which may indicate complications of diabetic retinopathy. A target feature map indicating target features classified as clinically significant is obtained as an outcome of the machine learning model. The target feature map includes attributes of the target features, such as location, and/or size and/or shape of each detected target feature. The target feature map is analyzed with respect to one or more sample feature maps that includes sample features classified as clinically significant. The sample feature map(s) are obtained as an outcome of the same machine learning model fed one or more sample medical images. The sample medical image(s) is captured by the same specific medical imaging sensor and/or the same specific setup of the same (or another) imaging sensor.

The analysis may be performed, for example, by a feature matching process that maps target features of the target feature map to corresponding sample features of the sample feature map. One or more target features depicted in the target feature map having attributes matching sample feature(s) depicted in the sample feature map are identified. The identified target feature(s) may be in the same location in both the target feature map and in the sample feature map. The identified target feature(s) of the target feature map, which has been classified by the machine learning model as clinically significant, is re-classified (e.g., designated) as an artifact that is unrelated to the subject depicted in the target image and is of no clinical significance, for example, a speck of dust on the lens of the camera that captured the target medical image (and the sample medical image(s)). The identified target feature is re-classified as artifact, since the target medical image and the sample medical image(s) are of different subjects and/or of different body parts (optionally of the same subject, such as left eye and right eye), the probability of the same clinically significant features having matching attributes and appearing in both images is very low, in particular, probability of the same clinically significant features appearing at the same location in both the medical and sample medical image(s). The identified target feature which is found in both the target medical image and the sample medical image(s) is likely due to a factor of the medical imaging device itself (e.g., speck of dust on the lens, scratch on the lens) and/or a factor external to the patient (e.g., lighting).

At least some embodiments described herein address the technical problem of detecting artifacts in medical images. At least some embodiments described herein improve the technical field of medical image analysis, optionally, of a computerized process that uses a machine learning models.

Artifacts in medical images may be difficult to distinguish from clinically significant features. Such artifacts are the main source of human error in retinal image analysis, for example, color images of the fundus, such as used for screening for diabetic retinopathy. Since some visual artifacts have characteristics that are similar to anatomical features, the artifact may be confused with a real retinal disease anatomical feature. In retinal images, clinically significant features, for example, aneurysm, hemorrhage, exudate, and artifacts, for example, due to a speck of dust on a lens of the camera capturing the image, is difficult. A large percentage of the retinal image analysis human errors are due to the inability of the human reader to differentiate between an actual lesion in the image that is associated with the disease and a visual artifact.

Prior approaches have attempted to use machine learning models trained to identify clinically significant medical features. However, such machine learning models may fail to distinguish between clinically significant medical features and artifacts. The machine learning model may incorrectly identify detected artifacts as clinically significant features.

At least some embodiments described herein provide a technical solution to the above mentioned technical problem, and/or improve the above mentioned technical field, by providing an approach to re-classify one or more of the clinically significant features of a target medical image found by the machine learning model, as artifacts. The approach is based on comparing the target features found by the machine learning model to sample features found by the same machine learning model fed sample images. The sample images are captured by the same imaging device used to capture the target images, and/or the sample image are captured using the same setup of the imaging device used to capture the sample image. However the sample images depict a sample subject that is different than the target subject depicted in the target images. Alternatively, the sample images may depict a different body region of the same subject depicted in the target image, for example, the sample image depicts the left retina of the subject and the target image depicts the right retina of the subject. Now, artifacts caused by the imaging device itself, for example, speck of dust on the lens, and/or artifacts caused by factors external to the subject, for example, bad lighting, are predicted to appear at the same place and/or to appear the same on both the sample image(s) and the target image. Clinically significant features, which are found by the machine learning model at the same location and/or that appear the same, on both the target image and the sample medical image, are designated as artifacts.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
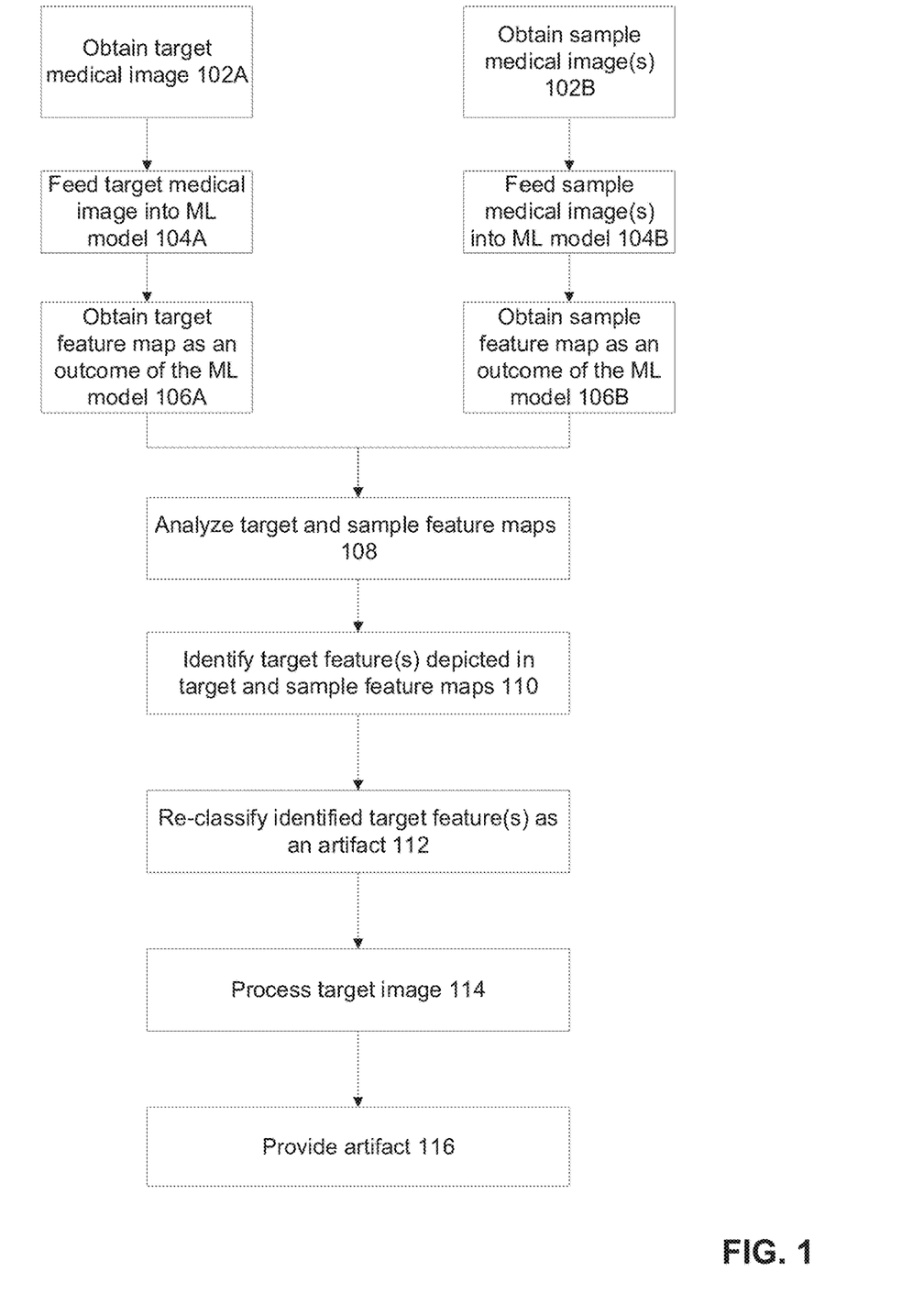
FIG. 1 is a flowchart of a method for detection of artifacts in medical images by identifying target features, in accordance with some embodiments of the present invention.
Figure 2:
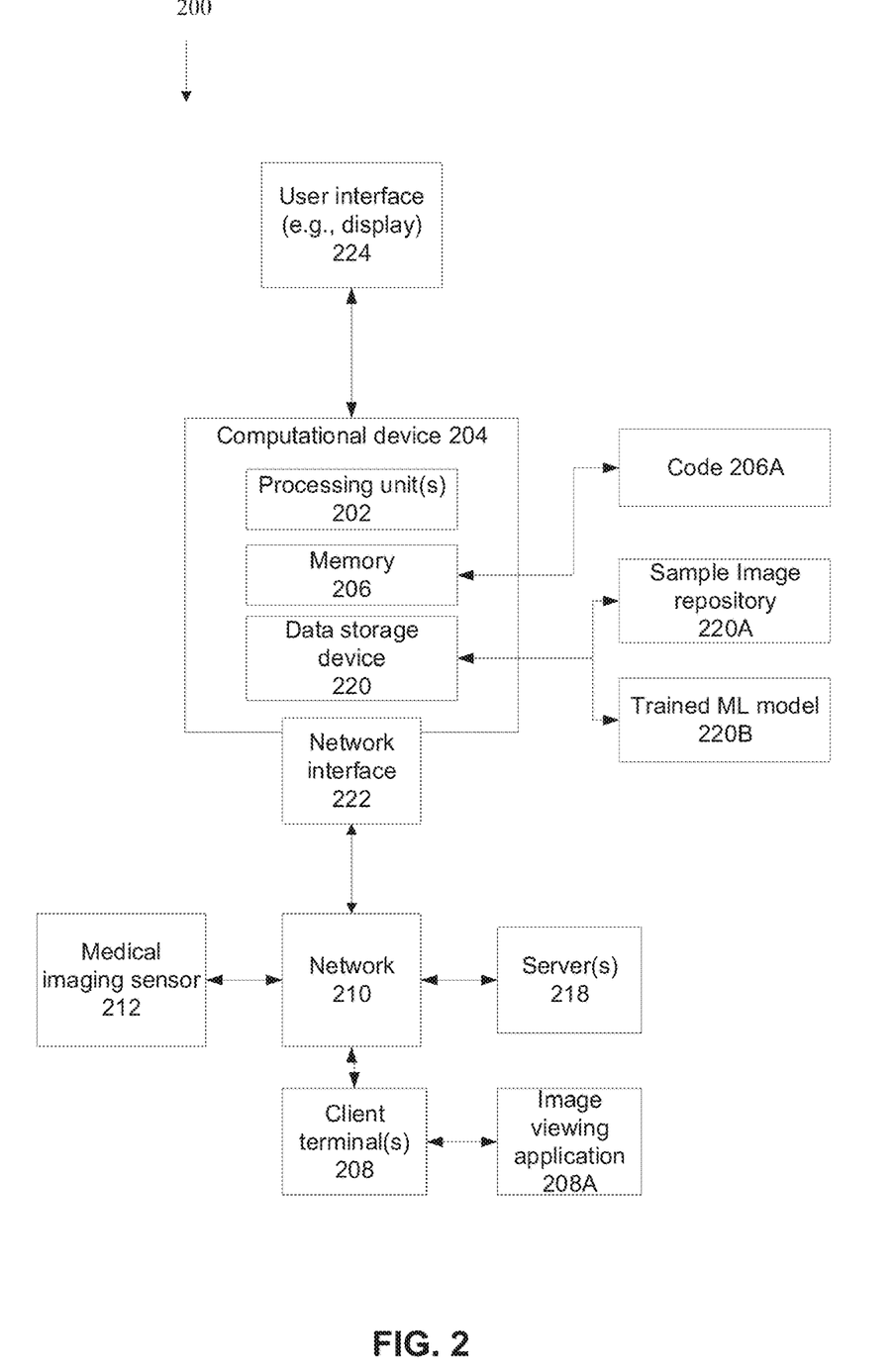
FIG. 2 is a block diagram of components of a system for detection of artifacts in medical images by identifying target features, in accordance with some embodiments of the present invention.

Reference is now made to FIG. 1, which is a flowchart of a method for detection of artifacts in medical images by identifying target features, in accordance with some embodiments of the present invention. Reference is also made to FIG. 2, which is a block diagram of components of a system 200 for detection of artifacts in medical images by identifying target features, in accordance with some embodiments of the present invention. System 200 may implement the features of the method described with reference to FIG. 1, by one or more hardware processors 202 of a computing device 204 executing code instructions stored in a memory (also referred to as a program store) 206.

Computing device 204 may be implemented as, for example, a client terminal, a server, a virtual machine, a virtual server, a radiology workstation, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a radiology workstation for enabling the user to view the identified artifacts with the target image, for example, as an overlay.

Multiple architectures of system 200 based on computing device 204 may be implemented. For example:

In an exemplary centralized implementation, computing device 204 storing code 206A may be implemented as one or more servers (e.g., network server, web server, a computing cloud, a virtual server) that provides services (e.g., one or more of the acts described with reference to FIG. 1) to one or more servers 218 and/or client terminals 208 over a network 210, for example, providing software as a service (SaaS) to the servers 218 and/or client terminal(s) 208, providing software services accessible using a software interface (e.g., application programming interface (API), software development kit (SDK)), providing an application for local download to the servers 218 and/or client terminal(s) 208, and/or providing functions using a remote access session to the servers 218 and/or client terminal(s) 208, such as through a web browser and/or viewing application and/or as an add-on to a medical imaging viewer application. For example, users use client terminals 208 to access computing device 204 to provide one or more target images captured by a medical imaging sensor 212. Computing device 204 centrally feeds each target image into a trained ML model 220B to obtain a target feature map of clinically significant features. The target feature map is compared to sample feature maps of sample images (e.g., held in sample image repository 220A) captured by the same medical imaging sensor 212 and/or using the same setup of sensor 212, fed into ML model 220B. Features at the same location and/or same size and/or same shape are designed as artifacts. The indication of the identified artifacts is provided to each respective client terminal 208.

In another example, in a local implementation, computing device 204 may serve as a local client terminal, or code 206A may be an add-on to a process running on computing device (e.g., PACS), or computing device 204 may be integrated with medical imaging sensor 212 such as a radiology control station of the medical imaging sensor 212. Code 206A may be obtained from computing device 204 for local execution on client terminal 208 and/or on server 218.

Computing device 204 receives images captured by a medical imaging sensor 212.

Examples of medical imaging sensor(s) 212 include: a camera such a standard visible light sensors (e.g., CCD, CMOS sensors, and/or red green blue (RGB) sensor, black and white sensor) for example for capturing images of the retina (e.g., fundus), x-ray, ultrasound, infrared, short wave infrared (SWIR), thermal sensor, and the like.

Medical sensor 212 is used to capture the target medical image, and may be used to capture the sample medical images (e.g., stored in sample image repository 220A).

Sensor 212 may transmit captured target and/or sample images to computing device 204, for example, via a direct connected (e.g., local bus and/or cable connection and/or short range wireless connection), and/or via a network 210 and a network interface 222 of computing device 204 (e.g., where sensors are connected via internet of things (IoT) technology and/or are located remotely from the computing device).

Network interface 222 may be implemented as, for example, a wire connection (e.g., physical port), a wireless connection (e.g., antenna), a network interface card, a wireless interface to connect to a wireless network, a physical interface for connecting to a cable for network connectivity, and/or virtual interfaces (e.g., software interface, application programming interface (API), software development kit (SDK), virtual network connection, a virtual interface implemented in software, network communication software providing higher layers of network connectivity).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may store code 206A that execute one or more acts of the method described with reference to FIG. 1.

Computing device 204 may include data storage device 220 for storing data, for example, sample image repository 220A for storing sample medical images captured by imaging sensor 212 and/or for storing sample feature maps outcomes of ML model 220B fed the sample medical images, and/or for storing trained ML model 220B. Data storage device 220 may be implemented as, for example, a memory, a local hard-drive, a removable storage unit, an optical disk, a storage device, a virtual memory and/or as a remote server 218 and/or computing cloud (e.g., accessed over network 210).

Computing device 204 and/or client terminal(s) 208 include and/or are in communication with one or more physical user interfaces 224 that include a mechanism for inputting data and/or for viewing data, for example, a display for presenting the target image and identified artifacts. Exemplary user interfaces 224 include, for example, one or more of, a touchscreen, a display, a keyboard, a mouse, and voice activated software using speakers and microphone.

Client terminal(s) 208 may be implemented as, for example, a radiology workstation, a desktop computer (e.g., running a PACS viewer application), a mobile device (e.g., laptop, smartphone, glasses, wearable device), and another medical image station server.

Server 218 may be implemented as, for example, an image server storing sample image repository 220A. Server 218 may store trained ML model 220B, which may be remote accessed by computing device 204. For example, computing device 204 provides the target image and/or sample images to server 218 over network 210, and obtains the target feature map and/or sample feature map(s) from server 218 (i.e., server 218 locally feeds the images into ML model 220B). In another implementation, ML model 220B is trained by server 218, and provide to computing device 204 for local implementation.

At 102A, a target medical image is obtained. The target medical image is captured by a specific medical imaging sensor at a specific setup. The specific setup may be, for example, orientation of the sensor relative to the subject, location of the sensor relative to the subject, and/or parameters of the sensor (e.g., intensity, focus, aperture, exposure time).

The target medical image may be, for example:
A retinal color (e.g., fundus) image, such as for diabetic retinopathy screening.
An image of skin, such as for screening for melanoma.
A chest x-ray.
An ultrasound image.

At 104A, the target medical image is fed into a machine learning model. The machine learning model may be trained on a training dataset, for example, of medical images annotated with clinically significant features. The machine learning model is trained on the training dataset for generating an outcome of identified clinically significant features on an inputted image.

The ML model may be implemented as, for example, a neural network of various architectures (e.g., convolutional, fully connected, deep, encoder-decoder, recurrent, graph), support vector machines (SVM), logistic regression, k-nearest neighbor, decision trees, boosting, random forest, a regressor, and/or a combination of multiple sub-architectures, for example, integrated networks, parallel networks, and/or cascade networks. and/or any other commercial or open source package allowing regression, classification, dimensional reduction, supervised, unsupervised, semi-supervised or reinforcement learning. The Machine learning model may be trained using supervised approaches and/or unsupervised approaches.

In an example, the ML model is a neural network trained to identify retinal lesions on an inputted retinal color image. Exemplary retinal lesions include: hard exudate, neovascularization on disk (NVD), neovascularization elsewhere (NVE), intraretinal microvascular abnormality (IRMA), venous bleeding, microaneurysm, and blot hemorrhage.

It is noted that artifacts such as a speck of dust on the lens of the camera capturing the target (e.g., retinal) image is difficult to differentiate from the exemplary clinically significant feature (e.g., retinal lesions) identified by the ML model. The ML model incorrectly identifies the speck of dust (or other artifact such as a scratch on the lens) as a retinal lesion (or other clinically significant feature).

At 106A, a target feature map of target features is obtained as an outcome of the machine learning model. The target feature map denotes the target features determined by the ML model to be clinically significant features.

The target feature map indicates attributes of each target feature. Exemplary attributes include a location and a size and/or a shape of each respective target feature identified by the machine learning model.

The target feature map may be implemented as an image depicting only the target features, where the pixels of the image may correspond 1:1 to pixels of the target image. Other examples of implementation of the target feature map include bounding boxes on the target image delineating respective features, segmentations on the target image delineating respective features applied to the target medical image, and identified pixels of the target medical image delineating respective features (e.g., list of x,y coordinates of the pixels, and/or as a mask with pixels of the mask denoting the target features).

The target feature map may be implemented as a dataset indicating a descriptor of the respective feature, including a visual description of what the feature looks like, and a location of the feature within the image (e.g., x,y coordinates).

The target feature map may be outputted by a final layer of the ML model. In another implementation, the target feature map is extracted from one or more hidden layers of a neural network implementation of the machine learning model.

At 102B, one or more sample images are obtained.

The sample image(s) are obtained by the same medical imaging sensor used to capture the target image (i.e., the same physical piece of hardware). Alternatively or additionally, the sample image(s) are obtained using a setup that matches the setup used to capture the target image, where the medical imaging may be similar (i.e., a different physical piece of hardware, but of the same model) or the same (i.e., the same physical piece of hardware).

The sample medical image(s) may depict subject(s) that are different than the subject depicted in the target medical image The sample medical image(s) may depict different body parts of the same depicted in the target medical image. For example, the target medical image depicts a first body portion of a subject, and the sample medical image depicts a second body portion of the subject. For example, the target medical image depicts a left retina of a left eye of a subject, and the sample medical image(s) depict a right retina of a right eye of the same subject.

At 104B, the sample image(s) are fed into the ML model. The ML model is the same ML model as described with reference to 104A.

At 106B, sample feature maps are obtained as outcomes of the ML model. The sample feature map(s) includes sample features classified as clinically significant by the machine learning model.

The format and/or implementation of the sample feature maps is the same as the format and/or implementation of the target feature map described with reference to 106A.

At 108, the target feature map is analyzed with respect to the sample feature map(s).

The analysis is done by comparing the target feature map with the sample feature map, to identify a common feature (s) appearing at a same location in the target feature map and in the sample feature map(s), and/or common feature(s) having a same shape and/or same size in the target feature map and in the sample feature map(s).

The analysis may be done by comparing attributes of the target features with attributes of the sample features to find target feature(s) having attributes that match attributes of sample feature(s).

The comparison may be performed in different ways. For example, checking each target feature of the target feature map against the same location in the sample feature map, to determine whether a feature of a same size and/or shape exists at the same location. In another example, when the feature maps are implemented as images (e.g., image of only the features, image with the features marked thereon), the image of the target feature map may be compared with the image(s) of the sample feature map to identify common features at a same location and/or same shape and/or same size in the image of the target feature map and in the image(s) of the sample feature map. The comparison of the images may be done, for example, by applying a feature matching process to the image of the target feature map and to the image(s) of the sample feature map, to identify the common features at the same location and/or same orientation and/or same size and/or same shape.

It is noted that the accuracy of the analysis, i.e., the probability of correctly designating a target feature as an artifact, increases with increasing number of sample feature maps. This is since as the number of sample feature maps increases, it becomes increasingly highly unlikely that the same target feature of the target image will be found in the same location and/or having the same size and/or same shape, in all of the sample feature maps of all the sample images.

At 110, target feature(s) depicted in the target feature map and depicted in the sample feature map are identified. Target features having attributes that match attributes of sample features may be identified.

The target feature is identified when a specific feature of the target feature map has a same location, and a same size and/or a same shape, as a corresponding sample feature depicted in the sample feature map(s).

At 112, the identified target feature(s) depicted in the target medical image, which has been previously classified by the machine learning model as clinically significant, is re-classified as an artifact, i.e., of no clinical significance, and/or of being unrelated to the subject depicted in the tissue but due to an external factor. For example, using a metadata tag, classification label, visual marking, storage in a dataset, and the like.

Examples of factors depicted in the target image that cause the clinically significant features detected by the ML model to be identified as target feature(s) which are designated as artifacts include: light reflected from an eye into a camera capturing the target medical image, dirt on a lens of the camera, malfunction of the specific medical imaging sensor, and lighting problem captured by the specific medical imaging sensor.

Optionally, other target features that were not identified as artifacts are designated as clinically significant features, or an initial designation as clinically significant features made by the ML model may be maintained.

At 114, additional processing may be performed on the target image, for example, in preparation for presentation.

A visual indication of the identified target feature(s) designated as artifact may be prepared and/or instruction may be generated accordingly. The visual indication may be, for example, a border surrounding the artifact, an arrow pointing to the artifact, changing colors of the pixels of the artifact to a color that does not appear in the image, an overlay, and presenting a text message. Alternatively or additionally, the target medical image may be processed for removing the artifact. The artifact may be removed, for example, by replacing the artifact with a benign feature not identifiable by the machine learning model as a clinically significant feature. The replacement may be done, for example, by a generative adversarial network, or by another machine learning model.

At 116, the medical image and/or the artifact (e.g., visual representation thereof), or the processed image with removed artifact, is provided, for example, for presentation on a display, storage (e.g., in the PACS), and/or further processing (e.g., by an automated diagnosis application).

Figure 3:
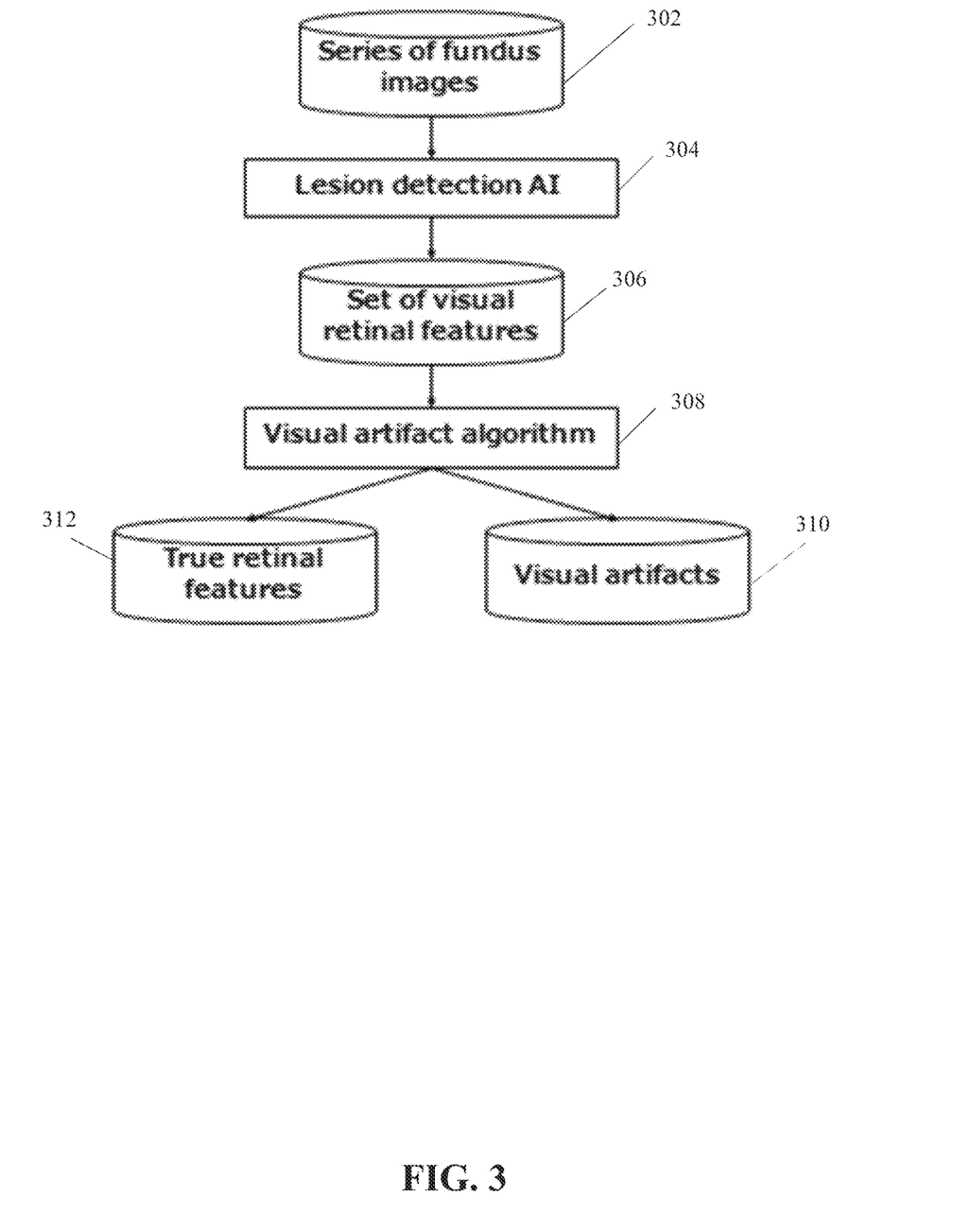
FIG. 3 is a flowchart of a method of identifying artifacts in fundus images, in accordance with some embodiments of the present invention.

Reference is now made to FIG. 3, which is a flowchart of a method of identifying artifacts in fundus images, in accordance with some embodiments of the present invention. Features of the method described with reference to FIG. 3 may be implemented using features of the method described with reference to FIG. 1, and/or using components of system 200 described with reference to FIG. 2.

At 302, a series of fundus images are obtained. The fundus images include target images (e.g., as described with reference to 102A of FIG. 1) and sample images (e.g., as described with reference to 102B of FIG. 1) of another eye of the same subject and/or of different subjects.

At 304, the series of fundus images are fed into a lesion detection artificial intelligence (AI) process, i.e., ML model, for example, as described with reference to 104A-B of FIG. 1.

At 306, a set of visual retinal features is obtained for each of the fundus images, as an outcome of the ML model, for example, as described with reference to 106A-B of FIG. 1. Target visual retinal features are obtained for the target fundus images, and sample visual retinal features are obtained for the sample fundus images.

At 308, a visual artifact process is applied for analyzing the target visual retinal features in comparison to the sample visual retinal features, for example, as described with reference to 108-110 of FIG. 1.

At 310, target visual retinal features that appear in both the target image and in the sample image(s), at the same location, and having a same size and/or shape, are designated as visual artifacts. Such as artifacts may be, for example, due to dust and/or scratch on the lens of the camera that captured the target and sample images. For example, as described with reference to 112 of FIG. 1

At 312, target visual retinal features that are not designated as artifacts are designated as true retinal features.

Figure 4:
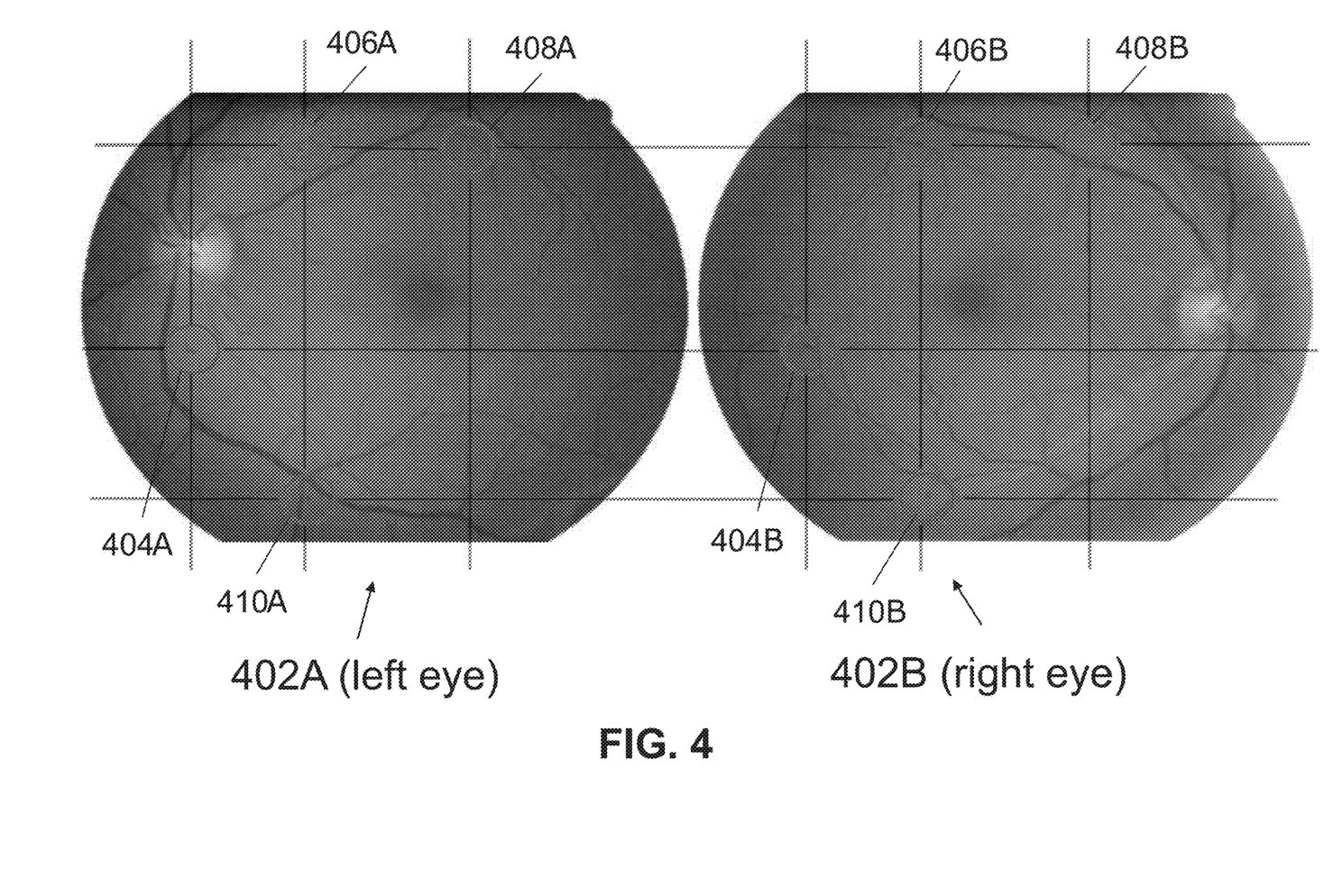
FIG. 4 includes an exemplary target image and a sample image, with identified artifacts, in accordance with some embodiments of the present invention.

Reference is now made to FIG. 4, which depicts an exemplary target image 402A and a sample image 402B, with identified artifacts 404A, 406A, 408A, and 410A, in accordance with some embodiments of the present invention. Target image 402A depicts a retinal image of a left eye of a subject. Sample image 402B depicts a retinal image of a right eye of the same subject (or another subject). Features 404A-B, 406A-B, 408A-B, and 410A-B may be identified as clinically significant retinal features by feeding images 402A and 402B into a ML model trained to identify retinal features in retinal images. Target features 404A, 406A, 408A, and 410A of image 402A correspond to 404B, 406B, 408B, and 410B of image 402B, appearing at the same location within each respective image, as designated as artifacts. For example, feature 404A is located at the same location as feature 404B. Since the two images are of different eyes, the same feature is not expected to be located at the same location, indicating that the problem is not with the eye depicted in the image, but due to an external factor, such as dust on the lens.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant imaging sensors and ML models will be developed and the scope of the terms imaging sensor and ML model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of re-classifying a clinically significant feature of a medical image as an artifact, comprising:
   feeding a target medical image captured by a specific medical imaging sensor at a specific setup into a machine learning model;
   obtaining a target feature map as an outcome of the machine learning model,
   wherein the target feature map includes target features classified as clinically significant by the machine learning model;
   analyzing the target feature map with respect to at least one sample feature map obtained as an outcome of the machine learning model fed a sample medical image captured by at least one of: the same specific medical imaging sensor and the same specific setup,
   wherein the at least one sample feature map includes sample features classified as clinically significant by the machine learning model;
   identifying at least one target feature depicted in the target feature map having attributes matching at least one sample feature depicted in the at least one sample feature map; and
   re-classifying as an artifact, the identified at least one target feature depicted in the target medical image and classified as clinically significant by the machine learning model.

2. The computer implemented method of claim 1, wherein the target medical image and the sample medical images are at least one of: of different subjects, of different body parts of the same subject.

3. The computer implemented method of claim 1, wherein the target feature map indicates attributes of each target feature identified by the machine learning model, the attributes including at least one of: (i) a location and (ii) at least one of a size and a shape of the respective target feature.

4. The computer implemented method of claim 3, wherein the at least one target feature is identified when a specific feature of the target feature map has a same location, and at least one of a same size and a same shape, as a corresponding sample feature depicted in the at least one sample feature map.

5. The computer implemented method of claim 1, wherein the target feature map is extracted from a hidden layer of a neural network implementation of the machine learning model.

6. The computer implemented method of claim 1, wherein the target feature map comprises at least one of: bounding boxes delineating respective features, and segmentations delineating respective features applied to the target medical image, and identified pixels of the target medical image delineating respective features.

7. The computer implemented method of claim 1, wherein analyzing comprises comparing the target feature map with the at least one sample feature map to identify a common feature appearing at a same location in the target feature map and in the at least one sample feature map.

8. The computer implemented method of claim 1, wherein the target feature map is implemented as an image, and analyzing comprises comparing the image of the target feature map with at least one sample image of the at least one sample feature map to identify common features at a same location in the image of the target feature map and in the at least one sample image of the at least one sample feature map.

9. The computer implemented method of claim 8, wherein the comparing comprises applying a feature matching process to the image of the target feature map and to the at least one sample image of the at least one sample feature map, to identify common features at the same location and same orientation.

10. The computer implemented method of claim 1, wherein the identified at least one target feature re-classified as artifact is selected from a group consisting of: light reflected from an eye into a camera capturing the target medical image, dirt on a lens of the camera, malfunction of the specific medical imaging sensor, lighting problem captured by the specific medical imaging sensor.

11. The computer implemented method of claim 1, wherein the target medical image comprises a retinal color fundus image, the specific medical imaging sensor comprises a camera, the machine learning model is trained to identify retinal lesions, and the clinically significant features include retinal lesion.

12. The computer implemented method of claim 11, wherein the retinal lesions are selected from a group comprising: hard exudate, neovascularization on disk (NVD), neovascularization elsewhere (NVE), intraretinal microvascular abnormality (IRMA), venous bleeding, microaneurysm, and blot hemorrhage.

13. The computer implemented method of claim 1, wherein the target medical image depicts a first body portion of a subject, and the sample medical image depicts a second body portion of the subject.

14. The computer implemented method of claim 13, wherein the first body portion of the subject comprises a first eye of the subject, and the second body portion of the subject comprises a second eye of the subject.

15. The computer implemented method of claim 1, further comprising designating non-identified at least one target feature of the target feature map as clinically significant features.

16. The computer implemented method of claim 1, further comprising visually marking the identified at least one target feature designated as the artifact on the target medical image presented on a display.

17. The computer implemented method of claim 1, further comprising processing the target medical image identified as the artifact for removing the identified at least one target feature from the medical image.

18. The computer implemented method of claim 17, wherein processing comprises replacing the identified at least one target feature of the target medical image identified as the artifact with a benign feature not identifiable by the machine learning model as a clinically significant feature.

19. A device for re-classifying a clinically significant feature of a medical image as an artifact, comprising:
- at least one hardware processor executing a code for:
  - feeding a target medical image captured by a specific medical imaging sensor at a specific setup into a machine learning model;
  - obtaining a target feature map as an outcome of the machine learning model,
  - wherein the target feature map includes target features classified as clinically significant by the machine learning model;
  - analyzing the target feature map with respect to at least one sample feature map obtained as an outcome of the machine learning model fed a sample medical image captured by at least one of: the same specific medical imaging sensor and the same specific setup,
  - wherein the at least one sample feature map includes sample features classified as clinically significant by the machine learning model;
  - identifying at least one target feature depicted in the target feature map having attributes matching at least one sample feature depicted in the at least one sample feature map; and
  - re-classifying as an artifact, the identified at least one target feature depicted in the target medical image and classified as clinically significant by the machine learning model.

20. A non-transitory medium storing program instructions for re-classifying a clinically significant feature of a medical image as an artifact, which, when executed by a processor, cause the processor to:
- feed a target medical image captured by a specific medical imaging sensor at a specific setup into a machine learning model;
- obtain a target feature map as an outcome of the machine learning model,
- wherein the target feature map includes target features classified as clinically significant by the machine learning model;
- analyze the target feature map with respect to at least one sample feature map obtained as an outcome of the machine learning model fed a sample medical image captured by at least one of: the same specific medical imaging sensor and the same specific setup,
- wherein the at least one sample feature map includes sample features classified as clinically significant by the machine learning model;
- identify at least one target feature depicted in the target feature map having attributes matching at least one sample feature depicted in the at least one sample feature map; and
- re-classify as an artifact, the identified at least one target feature depicted in the target medical image and classified as clinically significant by the machine learning model.

* * * * *